US012778500B2

(12) United States Patent
Wingren et al.

(10) Patent No.: US 12,778,500 B2
(45) Date of Patent: Nov. 3, 2026

(54) ESTIMATING AN ACTUAL LIGHT PROFILE FOR AN INDIVIDUAL

(71) Applicant: Brainlit AB, Lund (SE)

(72) Inventors: Tord Wingren, Lomma (SE); Bengt Lindoff, Bjarred (SE)

(73) Assignee: Brainlit AB, Lund (SE)

( * ) Notice: Subject to any disclaimer, the term of this patent is extended or adjusted under 35 U.S.C. 154(b) by 192 days.

(21) Appl. No.: 18/575,616

(22) PCT Filed: Jun. 28, 2022

(86) PCT No.: PCT/EP2022/067780
§ 371 (c)(1),
(2) Date: Dec. 29, 2023

(87) PCT Pub. No.: WO2023/275081
PCT Pub. Date: Jan. 5, 2023

(65) Prior Publication Data
US 2024/0324954 A1 Oct. 3, 2024

(30) Foreign Application Priority Data
Jun. 30, 2021 (EP) .................................... 21182687

(51) Int. Cl.
*A61B 5/00* (2006.01)
*A61B 5/0205* (2006.01)
*G16H 50/20* (2018.01)

(52) U.S. Cl.
CPC ........ *A61B 5/4857* (2013.01); *A61B 5/02055* (2013.01); *A61B 5/4836* (2013.01); *A61B 5/7246* (2013.01); *A61B 5/7267* (2013.01); *G16H 50/20* (2018.01)

(58) Field of Classification Search
CPC ... A61B 5/7246; A61B 5/7267; A61B 5/4857; A61B 5/02055; A61B 5/4836
See application file for complete search history.

(56) References Cited

U.S. PATENT DOCUMENTS

2020/0345969 A1* 11/2020 Choi ...................... G16H 20/40

FOREIGN PATENT DOCUMENTS

WO WO-2019101778 A1 * 5/2019 ......... H05B 47/1965

OTHER PUBLICATIONS

International Search Report from International Application No. PCT/EP2022/067780 mailed Jul. 14, 2022.

* cited by examiner

*Primary Examiner* — Boniface N Nganga
(74) *Attorney, Agent, or Firm* — Shih IP Law Group, PLLC

(57) ABSTRACT

The present inventive concept relates to a lighting system and a method for estimating an actual light profile for an individual. The method comprises: exposing the individual to a predetermined light stimuli using a lighting system; sensing a body response of the individual in response to the predetermined light stimuli; and estimating the actual light profile based on the sensed body response of the individual and the predetermined light stimuli.

20 Claims, 2 Drawing Sheets

ESTIMATING AN ACTUAL LIGHT PROFILE FOR AN INDIVIDUAL

TECHNICAL FIELD

The present inventive concept relates to a method and a lighting system for estimating an actual light profile for an individual.

BACKGROUND OF THE INVENTION

Chronobiology, which is a field of biology that studies timing (e.g., periodic) processes and phenomena in living organisms, is becoming increasingly more important for understanding human physiology. For example, the circadian rhythm is an internal process of living organisms (e.g. humans) that regulates the sleep-wake cycle. The circadian rhythm typically repeats over a time period which, for most people, is slightly longer than 24 hours. It is also known that this cycle can be different between different individuals. For example, some persons are known to be “morning” persons, while other are “evening” persons. Hence, the behavior at a certain time of day for different individual typically varies. This is usually referred to as a person’s chronotype.

An important part of chronobiology is the study of the impact of light on living organisms. It has, for example, been found that exposing a person to bright light in the evening can postpone the time that person falls asleep. Recent studies have further found that light can affect a person’s alertness and performance. Nowadays, light treatment is starting to be utilized by persons wanting to align their peak performance with an important event, for example an athlete wanting to perform the best in a competition. However, it has been found that the effect of light at a certain time of the day is not only instant, it also depends on the individual’s prior exposure to light during the day. For instance, in case an individual has been exposed to bright light in the morning (e.g., light similar to that of a bright summer’s morning), the effect of bright light during the afternoon is typically less than if the same person had spent the morning being exposed to light of lower illuminance (e.g. artificial light inside an office).

It is therefore important to know the light history of an individual. This is typically done by recording the light exposure of the individual using wearable light sensors. However, such solutions are prone to errors, since the individual may forget to put on the light sensor, or the sensor is worn incorrectly (e.g. being blocked by clothing). This results in an inaccurate light history, and, in turn, optimal light setting for the individual cannot be determined properly. Therefore, there exists a need for better knowledge regarding an individual’s light history.

CHANG ANNE-MARIE ET AL: “The human circadian system adapts to prior photic history”, THE JOURNAL OF PHYSIOLOGY, vol. 589, no. 5, 25 Feb. 2011 (2011-02-25), pages 1095-1102, demonstrates that prior photic history modulates (i) the phase resetting capacity and (ii) the magnitude of the melatonin suppression in response to a subsequent sub-saturating light exposure.

CHANG ANNE-MARIE ET AL: “Direct Effects of Light on Alertness, Vigilance, and the Waking Electroencephalogram in Humans Depend on Prior Light History”, SLEEP, vol. 36, no. 8, 1 Aug. 2013 (2013-08-01), pages 1239-1246, tests the hypothesis that prior exposure to very dim light compared to typical indoor light magnifies the alerting effect of a light stimulus during the biological night, as assessed by (a) subjective alertness, (b) neurobehavioral performance, and (c) spectral composition of the waking EEG.

HÉBERT MARC ET AL: “The effects of prior light history on the suppression of melatonin by light in humans”, JOURNAL OF PINEAL RESEARCH, vol. 33, no. 4, 1 Nov. 2002 (2002-11-01), pages 198-203, presents a study of the effect of a rapid (1 wk) change of light history on light sensitivity in humans.

CHELLAPPA S. L. ET AL: “Photic memory for executive brain responses”, PROCEEDINGS OF THE NATIONAL ACADEMY OF SCIENCES, vol. 111, no. 16, 22 Apr. 2014 (2014-04-22), pages 6087-6091, relates to the role of light for cognitive brain responses.

CATHERINE BEAULIEU ET AL: “Modulation of ERG retinal sensitivity parameters with light environment and photoperiod”, DOCUMENTA OPHTHALMOLOGICA, KLUWER ACADEMIC PUBLISHERS, DO, vol. 118, no. 2, 9 Jul. 2008 (2008-07-09), pages 89-99, relates to the relationship between the level of light exposure and retinal sensitivity to light.

SUAREZ ALEXIS ET AL: “Circadian Phase Prediction From NonIntrusive and Ambulatory Physiological Data”, IEEE JOURNAL OF BIOMEDICAL AND HEAL TH INFORMATICS, IEEE, PISCATAWAY, NJ, USA, vol. 25, no. 5, 27 Aug. 2020 (2020-08-27), pages 1561-1571, aims to build improved models for predicting circadian phase using data from minimally intrusive physiological sensors.

SUMMARY OF THE INVENTION

It is an object to, at least partly, mitigate, alleviate, or eliminate one or more of the above-identified deficiencies in the art and disadvantages singly or in any combination and solve at least the above-mentioned problem.

According to a first aspect a method for estimating an actual light profile for an individual is provided. The method comprising: exposing the individual to a predetermined light stimuli using a lighting system; sensing a body response of the individual in response to the predetermined light stimuli; and estimating the actual light profile based on the sensed body response of the individual and the predetermined light stimuli.

Within the context of this disclosure, the wording “actual light profile” should be construed as spectrally resolved information/data associated with an accumulated amount of light that the user has been exposed to during a certain time range (e.g. during the day, week, and/or month). Since the information/data is spectrally resolved, the actual light profile may comprise information of the amount of light at which wavelength/color the user has been exposed to. Put differently, the actual light profile may be the light history of the user.

Within the context of this disclosure, the wording “lighting system” should be construed as a lighting system designed to provide individuals (humans and/or animals) with light in accordance with their needs. An example of such lighting system is a BioCentric Lighting™ system provided by the applicant. The needs of the individuals may be given/defined in a target light profile (light recipe). The lighting system may, e.g., promote a wanted and/or healthy circadian rhythm of the user.

Within the context of this disclosure, the wording “body response” should be construed as a physical change of the individual in response to being exposed to the light stimuli. This may, for example, be a change of one or more of a body temperature, a skin color, a heart rate, a heart rate variation, a blood pressure, a respiration rate, and a melatonin level.

Within the context of this disclosure, the wording "in response to" should be construed as spanning a wide range of temporal ranges. For instance, some body responses, such as those listed above, may occur a short while (e.g. minutes and/or less than, or up to, one hour) after the individual being exposed to the light stimuli. Some body responses may occur a long time (e.g. hours and/or days) after the individual being exposed to the light stimuli. Put differently, the time span from the individual's exposure to the light stimuli that "in response to" refers to may vary between different body responses.

Within the context of this disclosure, the wording "light stimuli" should be construed as light at a specific intensity and having a specific spectral content. In particular, one or more wavelength ranges of the specific spectral content may induce a body response of the individual. As a specific example, it is known within the art that some wavelength ranges of blue light (e.g. 450 to 520 nm) stimulates increased cortisol levels and/or melatonin suppression for individuals being exposed to that light. In particular, the eyes of the individual have receptors sensitive to light within different wavelengths that may stimulate different body responses. Hence, when the individual is exposed to the predetermined light stimuli, it may be the eyes of the individual that are sensitive to the predetermined light stimuli, whereby the body response of the individual is stimulated.

By means of the present method, the actual light profile of the individual is estimated without requiring the individual to continuously wearing any external sensors (e.g. light sensors). The actual light profile may, in turn, allow the lighting system to expose the individual to more appropriate light in accordance with a target light profile (light recipe). In particular, the lighting system may be allowed to control light emitted by the lighting system to align the individual's actual light profile with the target light profile of the individual.

The method may further comprise determining a presence of the individual in an area serviced by the lighting system.

The act of exposing the individual to a predetermined light stimuli may comprise: varying over time at least one of an intensity and a spectral distribution of light emitted by the lighting system.

An associated advantage is that different types of body responses may be stimulated in the individual by exposing the individual to the predetermined light stimuli. This, since different body responses may be stimulated in the individual by changing the spectral distribution of light exposing the individual.

A further associated advantage is that the actual light profile may be determined with greater precision since a strength of a stimulated body response in the individual may depend on the intensity and/or the spectral distribution of light exposing the individual.

The act of sensing a body response of the individual in response to the predetermined light stimuli may comprise sensing a variation over time of one or more of: a body temperature; a skin color; a heart rate; a heart rate variation; a blood pressure; a respiration rate; and a melatonin level.

The act of estimating the actual light profile may comprise inputting data pertaining to the body response of the individual and data pertaining to the predetermined light stimuli into a machine learning model trained to correlate body responses of individuals and light stimuli to actual light profiles.

An associated advantage is that the trained machine learning model may be used to correlate body responses for individuals not forming part of a training set of individuals. Put differently, the lighting system may not need information of the body responses of the individual when estimating the actual light profile of the individual.

The machine learning model may be trained to correlate body responses of individuals, light stimuli, and identities of individuals to actual light profiles, and the method may further comprise: identifying the individual; and the act of estimating the actual light profile may further comprise inputting the identity of the individual into the machine learning model.

An associated advantage is that the estimation of the actual light profile for the individual may be enhanced, since the machine learning model is trained using data (i.e. body responses, light stimuli, identity) associated with the individual.

The machine learning model may be a convolutional neural network.

The act of estimating the actual light profile may comprise: identifying, in a database comprising entries correlating data pertaining to body responses of individuals and data pertaining to light stimuli to actual light profiles, an actual light profile corresponding to the sensed body response of the individual.

An associated advantage is that the estimation of the actual light profile for the individual may be implemented in a less complex manner.

A further associated advantage is that identifying the actual light profile in the database (e.g. by table lookup) may reduce computational costs associated with the estimation of the actual light profile.

The database may comprise entries correlating body responses of individuals, light stimuli, and identities of individuals to actual light profiles, and the method may further comprise: identifying the individual; and wherein the act of estimating the actual light profile may further comprise identifying an actual light profile corresponding to the identification of the individual and the sensed body response of the individual.

An associated advantage is that the estimation of the actual light profile for the individual may be enhanced since the database has information regarding the identities of individuals. Hence, it may allow for the identification of an actual light profile in the database which is associated with the individual.

According to a second aspect a lighting system is provided. The lighting system comprising: a central control server; one or more light sources; and a body response sensor configured to sense a body response; and wherein the central control server is configured to: control the one or more light sources to expose an individual to a predetermined light stimuli, receive, from the body response sensor, a body response of the individual in response to the predetermined light stimuli, and estimate an actual light profile based on the sensed body response of the individual and the predetermined light stimuli.

The above-mentioned features of the first aspect, when applicable, apply to this second aspect as well. In order to avoid undue repetition, reference is made to the above.

The central control server may be configured to control the one or more light sources to expose the individual to the predetermined light stimuli by being configured to: vary, over time, at least one of an intensity and a spectral distribution of light emitted by the one or more light sources.

The body response sensor may be configured to sense a variation over time of one or more of: a body temperature; a skin color; a heart rate; a heart rate variation; a blood pressure; a respiration rate; and a melatonin level.

The central control server may be configured to estimate the actual light profile by being configured to: input data pertaining to the body response of the individual and data pertaining to the predetermined light stimuli into a machine learning model trained to correlate body responses of individuals and light stimuli to actual light profiles.

The machine learning model may be trained to correlate body responses of individuals, light stimuli, and identities of individuals to actual light profiles, and the lighting system may further comprise: an identity sensor configured to determine an identity of the individual; and wherein the central control engine may be configured to estimate the actual light profile by being further configured to input the identity of the individual into the machine learning model.

The central control server may be configured to estimate the actual light profile by being configured to: identify, in a database comprising entries correlating data pertaining to body responses of individuals and data pertaining to light stimuli to actual light profiles, an actual light profile corresponding to the sensed body response of the individual.

The database may comprise entries correlating body responses of individuals, light stimuli, and identities of individuals to actual light profiles, and the lighting system may further comprise: an identity sensor configured to determine an identity of the individual; and wherein the central control engine may be configured to estimate the actual light profile by being further configured to identify an actual light profile corresponding to the identification of the individual and the sensed body response of the individual.

A further scope of applicability of the present disclosure will become apparent from the detailed description given below. However, it should be understood that the detailed description and specific examples, while indicating preferred variants of the present inventive concept, are given by way of illustration only, since various changes and modifications within the scope of the inventive concept will become apparent to those skilled in the art from this detailed description.

Hence, it is to be understood that this inventive concept is not limited to the particular steps of the methods described or component parts of the systems described as such method and system may vary. It is also to be understood that the terminology used herein is for purpose of describing particular embodiments only and is not intended to be limiting. It must be noted that, as used in the specification and the appended claim, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings do not exclude other elements or steps.

BRIEF DESCRIPTION OF THE DRAWINGS

The above and other aspects of the present inventive concept will now be described in more detail, with reference to appended drawings showing variants of the inventive concept. The figures should not be considered limiting the inventive concept to the specific variant; instead they are used for explaining and understanding the inventive concept. As illustrated in the figures, the sizes of layers and regions are exaggerated for illustrative purposes and, thus, are provided to illustrate the general structures of variants of the present inventive concept. Like reference numerals refer to like elements throughout.

DETAILED DESCRIPTION

The present inventive concept will now be described more fully hereinafter with reference to the accompanying drawings, in which currently preferred variants of the inventive concept are shown. This inventive concept may, however, be implemented in many different forms and should not be construed as limited to the variants set forth herein; rather, these variants are provided for thoroughness and completeness, and fully convey the scope of the present inventive concept to the skilled person.

An example scenario in which an actual light profile of an individual 130 is estimated will now be described with reference to FIG. 1A, FIG. 1B, and FIG. 2.

Figure 1A:
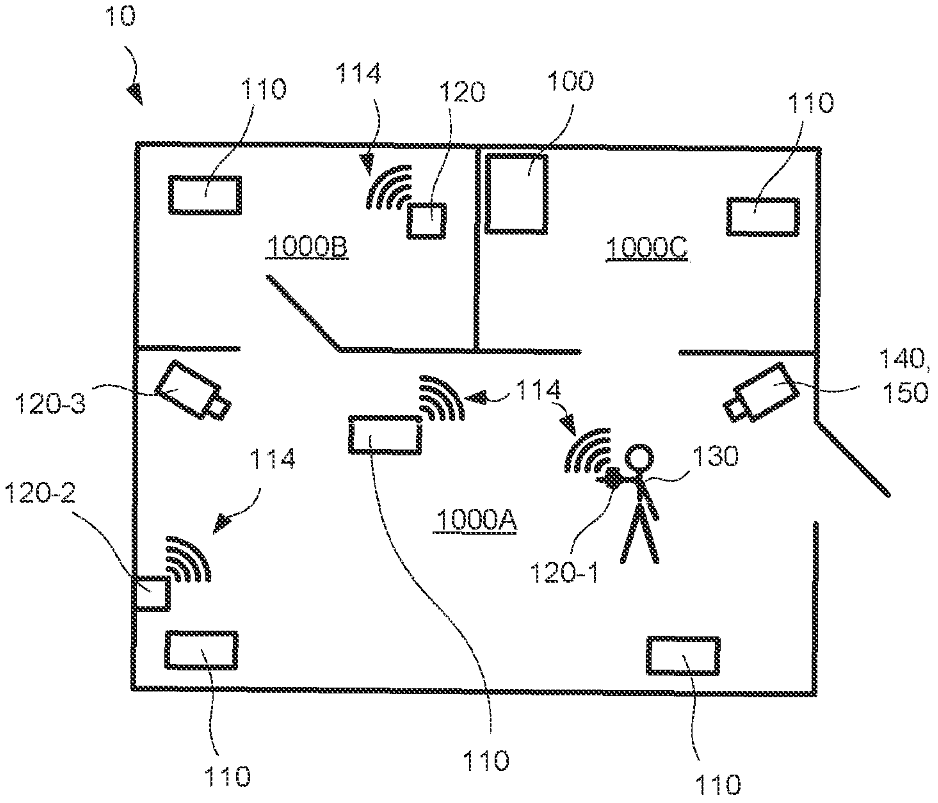
FIG. 1A illustrates a lighting system.
Figure 1B:
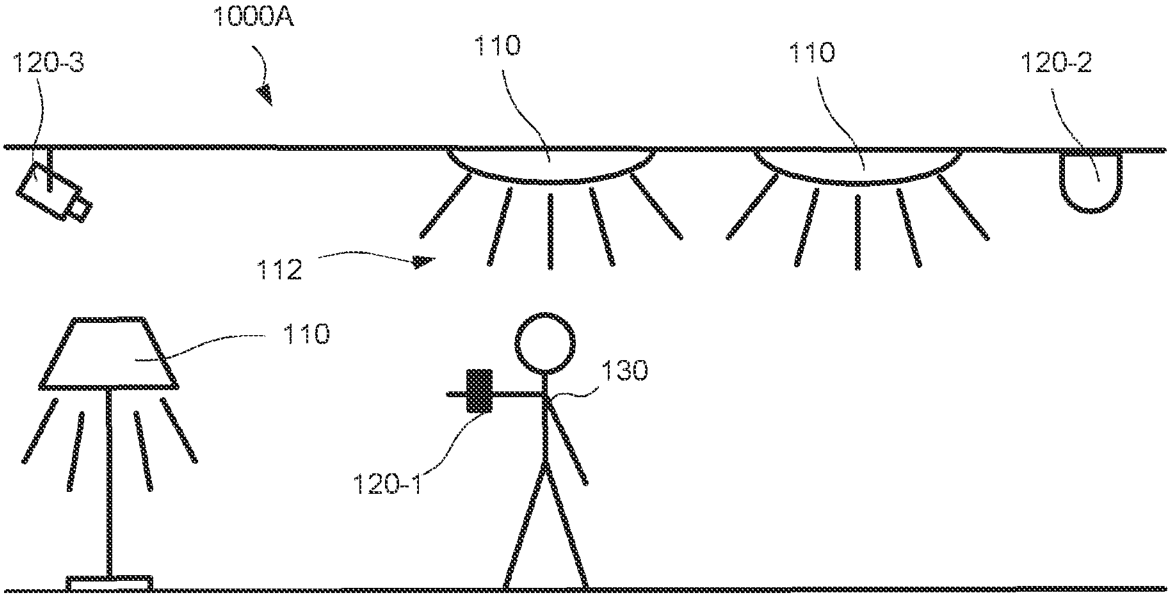
FIG. 1B illustrates a sideview of an area serviced by the lighting system of FIG. 1A.
Figure 2:
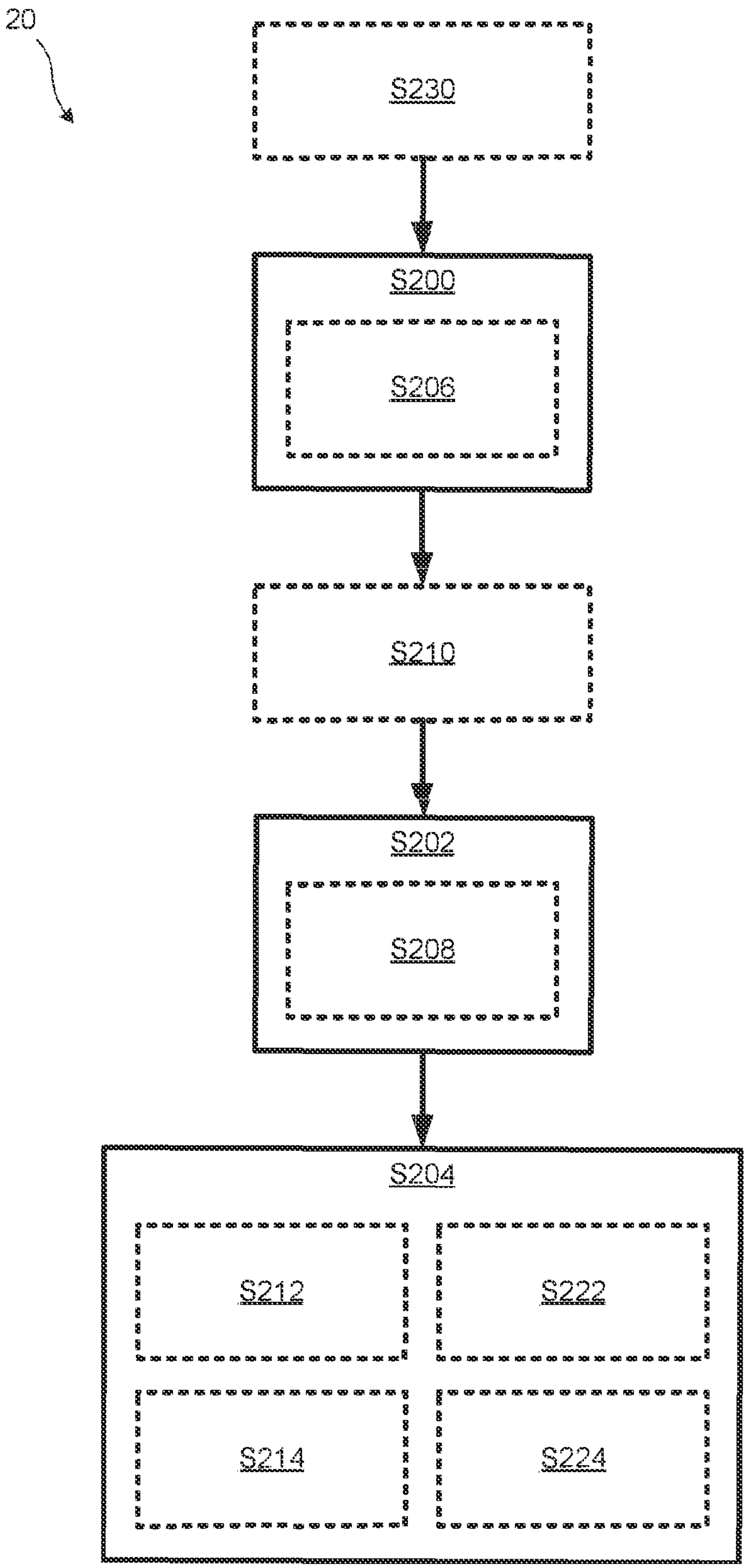
FIG. 2 is a block scheme of a method for estimating an actual light profile for an individual.

In the example scenario illustrated in FIG. 1A and FIG. 1B, the individual 130 is present in an area 1000A serviced by a lighting system 10. As is illustrated in FIG. 1A, the lighting system may service a plurality of different areas 1000A, 1000B, 1000C. The lighting system 10 comprises a central control server 100, one or more light sources 110, and at least one body response sensor 120. The lighting system 10 may further comprise a presence sensor 150 and/or an identity sensor 140. The central control server 100 may be located in the vicinity of the lighting system 10. The central control server 100 may be located at a location different from the lighting system 10. For example, the central control server 100 may be a cloud server and communicate with the other components/sensors/devices of the lighting system 10 via a network (e.g. the internet). The central control server 100 may comprise circuitry. The circuitry may comprise a transceiver. The circuitry may communicate with one or more of: the one or more light sources 110; the body response sensor 120; the presence sensor 150; and the identity sensor 140 via the transceiver. The transceiver may be configured to communicate using a wired and/or a wireless standard. For example, some light sources may communicate with the central control server 100 via a wired connection (e.g., USB, ethernet, etc.), while other light sources may communicate with the central control server 100 via a wireless connection (e.g. Wi-Fi, Bluetooth, etc.). This is illustrated in the example of FIG. 1A, where wireless connections are represented by symbol 114. However, wired connections are not shown in FIG. 1A in order to increase the legibility of that figure. The circuitry may comprise a processor and/or a non-transitory computer-readable storage medium. The processor may be a central processing unit (CPU). The non-transitory computer-readable storage medium may be configured to store program code portion which, when executed by the processor of the circuitry, performs one or more functions of the central control server 100. Put differently, the circuitry may be configured to perform one or more functions of the central control server 100. The non-transitory computer-readable medium may be configured to store data. For example, data relating to the other components (e.g. sensors) of the lighting system 10 and/or data associated with the individual 130. It is to be understood that some functions may be implemented by program code executed by the processor, while other functions are hardware implemented. Further, the circuitry may comprise a field-programmable gate array (FPGA) configured to perform one or more functions of the central control server 100.

The body response sensor 120 may be a portable electronic device. The body response sensor 120 may be a portable electronic device associated with the individual 130. For example, it may be a wearable health sensor, a smartwatch, a smartring, etc.). The body response sensor 120 may be an electronic device arranged to sense body responses of a plurality of individuals. The body response sensor 120 may be substantially stationary. For example, it may be a camera, a radar, an infrared camera, etc. Hence, it is to be understood that the lighting system 10 may comprise more than one body response sensor 120, and each sensor may be chosen depending on which body response is to be sensed. Relevant examples in this context may be body temperature, skin color, heart rate, heart rate variation, blood pressure, respiration rate, and melatonin level. In particular, the body response may be a change and/or a variation of the above examples. For example, the body response sensor 120 may be configured to determine a change of the color of the individual's skin. In the example illustrated in FIG. 1A, there are three body response sensors 120 in the area 1000A in which the individual 130 is present. In this example, the are a smartwatch 120-1, a radar 120-2, and a camera 120-3. The smartwatch 120-1 may, e.g., be configured to sense data associated with body temperature, skin color, heart rate, heart rate variation, blood pressure, and respiration rate. Data associated with the melatonin level of the individual 130 may be sensed by analyzing saliva from the individual 130. The radar 120-2 may, e.g., be configured to sense data associated with heart rate, heart rate variation, and respiration rate. The camera 120-3 may, e.g., be configured to sense data associated with skin color and respiration rate. The central control server 100 may be configured to analyze data from the body response sensor 120 to determine the body response of the individual 130. It is also envisioned that the body response sensor 120 may be arranged at the at least one light source 110. For example, the radar 120-2 may be arranged inside a light fixture housing the at least one light source 110.

The presence sensor 150 may be configured to determine S230 a presence of the individual 130 in the area 1000A serviced by the lighting system 10. The presence sensor 150 may be configured to sense data associated with the presence of the individual 130. The central control server 100 may be configured to determine S230 the presence of the individual 130 using the data associated with the presence of the individual 130. In the example of FIG. 1A, the presence sensor 150 is a camera. The camera 150 may be configured to directly detect (e.g., by using built-in processing capabilities for presence detection) the presence of the individual or communicate data associated with the presence of the individual 130 to the central control server 100. In that case, the central control server may be configured to determine the presence of the individual 130 using the data communicated from the presence sensor 150. The identity sensor 140 may be configured to determine an identity of the individual 130. The identity sensor 140 may be configured to sense data associated with the identity of the individual 130. The central control server 100 may be configured to identify S210 the individual 130 using the identity of the individual 130 and/or data associated with the identity of the individual 130. As illustrated in FIG. 1A, the presence sensor 150 and the identity sensor 140 may be the same sensor, which may, e.g., be a camera. Further, it is to be understood that the presence sensor 150 and/or the identity sensor 140 may be the same sensor as the body response sensor 120. Put differently, the camera 120-3 and the camera 140, 150 may be the same camera. The presence sensor 150 and/or the identity sensor 140 may, e.g., be a camera. It is to be understood that the presence sensor 150 and/or the identity sensor 140 may comprise a plurality of electronic devices configured to communicate with each other, and thereby determine the presence/identity of the individual 130. For example, the individual 130 may be associated with a first electronic device (e.g. a laptop, a computer, a smartphone, an RFID tag, a smartring, a smartwatch, etc.) and the presence and/or identity of the individual 130 may be determined when the electronic device is in range of and communicates with a second electronic device (e.g. a Bluetooth beacon, a Wi-Fi router, etc.).

The one or more light sources 110 may be arranged to illuminate the area serviced by the lighting system 10. An intensity and/or a spectral distribution of light emitted by the one or more light sources 110 may be adjustable. Each of the one or more light sources 110 may be individually adjustable. As is illustrated in FIG. 1B, the one or more light sources 110 may be arranged at the ceiling and/or as a floor lamp. It is further to be understood that the one or more light sources 110 may comprise light sources arranged on other places, such as on a wall.

The central control server 100 is configured to control the one or more light sources 110. In particular, the central control server 100 is configured to control the one or more light sources 110 to expose S200 the individual 130 to a predetermined light stimuli 112. This is illustrated in more detail in FIG. 1B. In FIG. 1B, the individual 130 is illustrated as standing below a light source 110 arranged at the ceiling of area 1000A. However, it is to be understood that the individual 130 may move around in the area 1000A and/or between different areas (such as the areas 1000A, 1000B, 1000C illustrated in FIG. 1A). Hence, it is to be understood that more than one light source may expose S200 the individual 130 to the predetermined light stimuli 112. The predetermined light stimuli 112 may be a predetermined combination of intensity and spectral distribution of light emitted by the one or more light sources 110. Further, different spectral ranges of light emitted by the one or more light sources 110 may have different intensities. Put differently, different colors of the light emitted by the one or more light sources 110 may have different intensities. The central control server 100 may be configured to control the one or more light sources 110 to, over time, expose S200 the individual 130 to a plurality of predetermined light stimuli.

The central control server 100 may be configured to control the one or more light sources 110 to expose S200 the individual 130 to the predetermined light stimuli 112 by being configured to vary S206, over time, at least one of an intensity and a spectral distribution of light emitted by the one or more light sources 110. The non-transitory computer-readable storage medium may comprise a control function configured to control the one or more light sources 110, and the processor of the circuitry executing the control function, thereby controlling the one or more light sources 110. The intensity and/or the spectral distribution of light emitted by the one or more light sources 110 may be varied according to a pre-determined pattern. The pre-determined pattern may be one or more of: decreasing intensity over a first time period; increasing intensity over a second time period; varying intensity in a periodical pattern between two values; emitting light of a first spectral distribution having a first intensity peak about a first peak wavelength, and slowly (e.g. over a time period from 1 to 30 minutes) changing to a emit light of a second spectral distribution having a second intensity peak about a second peak wavelength being different from the first peak wavelength.

The body response sensor 120 is configured to sense S202 a body response. The body response sensor 120 may be configured to sense data associated with a body response. The body response sensor 120 may be configured to sense S208 a variation over time of one or more of a body temperature, a skin color, a heart rate, a heart rate variation, a blood pressure, a respiration rate, and a melatonin level. The sensed body response may be a variation and/or change over time of one or more of a body temperature, a skin color, a heart rate, a heart rate variation, a blood pressure, a respiration rate, and a melatonin level. One or more of the body response sensors 120 illustrated in FIG. 1B may sense data associated with the body response of the individual 130 while the individual is exposed to the predetermined light stimuli 112. Further, one or more of the body response sensors 120 illustrated in FIG. 1B may sense data associated with the body response of the individual 130 after the individual has been exposed to the predetermined light stimuli 112. Furthermore, a smartwatch (as body response sensor 120) may be used to sense data associated with the body response when the individual 130 is not inside an area serviced by the lighting system 10.

The central control server 100 is further configured to receive, from the body response sensor 120, a body response of the individual 130 in response to the predetermined light stimuli 112. The central control server 100 may be further configured to receive, from the body response sensor 120, data associated with a body response of the individual 130 in response to the predetermined light stimuli 112. The central control server 100 may be further configured to determine a variation over time of one or more of a body temperature, a skin color, a heart rate, a heart rate variation, a blood pressure, a respiration rate, and a melatonin level. In that sense, the body response of the individual 130 may be the variation over time of one or more of a body temperature, a skin color, a heart rate, a heart rate variation, a blood pressure, a respiration rate, and a melatonin level. Some body responses may be detectable after a short-time exposure to the predetermined light stimuli 112, while other may require a longer-time exposure to the predetermined light stimuli 112. Further, some body responses may occur in direct connection (e.g. after a few minutes and/or up to an hour) with the exposure to the predetermined light stimuli 112. However, other body responses may occur hours and/or days after the exposure to the predetermined light stimuli 112. Hence, the predetermined light stimuli 112 may be constructed to stimulate a body response that may occur, more or less, in direct connection to or up to an hour after the exposure to the predetermined light stimuli 112. For example, one or more of body temperature, skin color, heart rate, heart rate variation, blood pressure, respiration rate, and melatonin level may be examples of body responses that may occur (e.g. by changing or varying over time) after a few minutes and/or up to an hour after exposure to the predetermined light stimuli 112 has begun.

The central control server 100 is further configured to estimate S204 an actual light profile based on the sensed body response of the individual 130 and the predetermined light stimuli 112. Since the individual 130 is exposed to the predetermined light stimuli 112, and the body response of the individual 130 depends on the individual's 130 previous exposure to light, the light history (i.e. the actual light profile) of the individual 130 can be inferred from the sensed body response and by knowing the composition of the predetermined light stimuli 112. Put differently, the actual light profile of the individual 130 can be estimated using data associated with the sensed body response of the individual 130 and data associated with the predetermined light stimuli 112. This data may be stored on the non-transitory computer-readable storage medium. In the following, two specific methods for estimating S204 the actual light profile of the individual 130 will be described.

A first method to estimate S204 the actual light profile may utilize machine learning. Hence, the central control server 100 may be configured to estimate S204 the actual light profile by being configured to input S212 data pertaining to the body response of the individual 130 and data pertaining to the predetermined light stimuli 112 into a machine learning model. The machine learning model may be trained to correlate body responses of individuals and light stimuli to actual light profiles. The machine learning model may be stored on the non-transitory computer-readable storage medium. The machine learning model may, e.g., be a convolutional neural network.

The machine learning model may be trained to correlate body responses of individuals, light stimuli, and identities of individuals to actual light profiles. The training of the machine learning model may be based on a training set of individuals. When collecting data to be used when training the machine learning model, each individual of the training set of individuals may have a known actual light profile. The training set of individuals may be exposed to at least one predetermined light stimuli, and their respective body responses (data associated with the body responses) are sensed. Preferably, several body responses may be sensed while collecting training data. Hence, it is to be understood that the training data may comprise more than one body response (or data relating to them). It is further to be understood that the training set of individuals may be exposed to the same predetermined light stimuli at a plurality of occasions at which each individual's present actual light profile is different. This procedure may then be repeated using different light stimuli. The training data may comprise the sensed body responses of the individuals, and the one or more predetermined light stimuli. The ground truth may comprise data associated with the actual light profiles associated with each of the individual of the training set of individuals. The machine learning model may then be trained to correlate the training data (body responses and predetermined light stimuli) to the ground truth (the actual light profiles).

The training data may further comprise the identity of each individual of the training set, and each actual light profile of the ground truth may be tagged/labelled with the identity of the individual that is associated with that actual light profile. In this case, the machine learning model may be trained to correlate body responses of individuals, light stimuli, and identities to actual light profiles. Thus, the central control engine may be configured to estimate S204 the actual light profile by being further configured to input S214 the identity of the individual 130 into the machine learning model. This may be advantageous in case the individual 130 is in the training set of individuals.

Even though it is not explicitly stated, the skilled person realizes that a trained machine learning model is validated using a validation set of individuals. The actual light profiles of the individuals of the validation set may be known, allowing for an unbiased evaluation of the trained machine learning model. A skilled person realizes that further sets of individuals (e.g. a test set) may be used to further evaluate and/or enhance the machine learning model.

A second method to estimate S204 the actual light profile may utilize a database. The database may comprise entries correlating data pertaining to body responses of individuals and data pertaining to light stimuli to actual light profiles. The entries of the database may further be correlating identities of the individuals. The database may be stored on the non-transitory computer-readable storage medium. The data of the entries of the database may be determined in a manner similar to that described in connection with the description of the training of the machine learning model. Hence, the central control server 100 may be configured to estimate S204 the actual light profile by being configured to identify S222 an actual light profile corresponding to the sensed body response of the individual 130 in a database. The database may comprise entries correlating body responses of individuals, light stimuli, and identities of individuals to actual light profiles. The central control engine may be configured to estimate S204 the actual light profile by being further configured to identify S224 an actual light profile corresponding to the identification of the individual 130 and the sensed body response of the individual 130.

The person skilled in the art realizes that the present inventive concept by no means is limited to the preferred variants described above. On the contrary, many modifications and variations are possible within the scope of the appended claims. For example, the individual 130 has been described as a human. However, it is to be understood that the present invention may be applied to other living beings as well, e.g., animals. Additionally, variations to the disclosed variants can be understood and effected by the skilled person in practicing the claimed invention, from a study of the drawings, the disclosure, and the appended claims.

The invention claimed is:

1. A method for estimating an actual light profile for an individual, wherein the actual light profile comprises spectrally resolved information associated with an accumulated amount of light that the individual has been exposed to during a previous time period, the method comprising:

exposing the individual to a predetermined light stimuli using a lighting system, wherein the act of exposing the individual to a predetermined light stimuli comprises: varying over time at least one of an intensity and a spectral distribution of light emitted by the lighting system;

sensing a body response of the individual in response to the predetermined light stimuli, wherein the act of sensing a body response of the individual in response to the predetermined light stimuli comprises sensing a variation over time of one or more of: a body temperature, a skin color, a heart rate, a heart rate variation, a blood pressure, a respiration rate, and a melatonin level; and wherein the method further comprises:

estimating the actual light profile based on the sensed body response of the individual and the predetermined light stimuli, wherein the act of estimating the actual light profile comprises inputting data pertaining to the body response of the individual and data pertaining to the predetermined light stimuli into a machine learning model trained to correlate body responses of individuals and light stimuli to actual light profiles.

2. The method according to claim 1, wherein the machine learning model is trained to correlate body responses of individuals, light stimuli, and identities of individuals to actual light profiles, the method further comprising:

identifying the individual; and wherein the act of estimating the actual light profile further comprises inputting the identity of the individual into the machine learning model.

3. The method according to claim 1, wherein the machine learning model is a convolutional neural network.

4. The method according to claim 1, wherein the machine learning model is trained to account for non-linear biological saturation effects, such that the magnitude of the body response to the predetermined light stimuli decreases as the accumulated amount of light in the previous time period increases.

5. The method according to claim 1, wherein estimating the actual light profile includes analyzing a time-dependent rate of change of the sensed body response in response to the light stimuli.

6. The method according to claim 1, wherein the sensed body response comprises at least two distinct types of physiological responses, and estimating the actual light profile comprises cross-correlating said at least two distinct types of physiological responses.

7. The method according to claim 1, wherein the body response is a variation in melatonin suppression or cortisol level stimulation.

8. The method according to claim 1, wherein the act of exposing the individual to the predetermined light stimuli comprises varying the intensity and spectral distribution according to a pre-determined pattern comprising slowly changing from a first spectral distribution having a first peak wavelength to a second spectral distribution having a second peak wavelength.

9. The method according to claim 1, wherein the machine learning model is trained using a training set of individuals having known actual light profiles, wherein each individual of the training set is exposed to the predetermined light stimuli at a plurality of different occasions associated with different actual light profiles.

10. The method according to claim 1, wherein estimating the actual light profile includes correlating the sensed body response to an unbiased ground truth comprising tagged actual light profile data.

11. A lighting system comprising:

a central control server;

one or more light sources; and a body response sensor configured to sense a body response, wherein the body response sensor is configured to sense a variation over time of one or more of: a body temperature, a skin color, a heart rate, a heart rate variation, a blood pressure, a respiration rate, and a melatonin level; and wherein the central control server is configured to:

control the one or more light sources to expose an individual to a predetermined light stimuli wherein the central control server is configured to control the one or more light sources to expose the individual to the predetermined light stimuli by being configured to: vary, over time, at least one of an intensity and a spectral distribution of light emitted by the one or more light sources, receive, from the body response sensor, a body response of the individual in response to the predetermined light stimuli, and estimate an actual light profile based on the sensed body response of the individual and the predetermined light stimuli, wherein the actual light profile comprises spectrally resolved information associated with an accumulated amount of light that the individual has been exposed to during a previous time period, and wherein the central control server is configured to estimate the actual light profile by being configured to: input data pertaining to the body response of the individual and data pertaining to the predetermined light stimuli into a machine learning model trained to correlate body responses of individuals and light stimuli to actual light profiles.

12. The lighting system according to claim 11, wherein the machine learning model is trained to correlate body responses of individuals, light stimuli, and identities of individuals to actual light profiles, the lighting system further comprising:

an identity sensor configured to determine an identity of the individual; and wherein the central control engine is configured to estimate the actual light profile by being further configured to input the identity of the individual into the machine learning model.

13. The lighting system according to claim 11, wherein the machine learning model is a convolutional neural network.

14. The lighting system according to claim 11, wherein the machine learning model is trained to account for non-linear biological saturation effects, such that the magnitude of the body response to the predetermined light stimuli decreases as the accumulated amount of light in the previous time period increases.

15. The lighting system according to claim 11, wherein to estimate the actual light profile includes to analyze a time-dependent rate of change of the sensed body response in response to the light stimuli.

16. The lighting system according to claim 11, wherein the sensed body response comprises at least two distinct types of physiological responses, and wherein to estimate the actual light profile comprises to cross-correlate said at least two distinct types of physiological responses.

17. The lighting system according to claim 11, wherein the body response is a variation in melatonin suppression or cortisol level stimulation.

18. The lighting system according to claim 11, wherein to expose the individual to the predetermined light stimuli comprises to vary the intensity and spectral distribution according to a pre-determined pattern that comprises to slowly change from a first spectral distribution having a first peak wavelength to a second spectral distribution having a second peak wavelength.

19. The lighting system according to claim 11, wherein the machine learning model is trained using a training set of individuals having known actual light profiles, wherein each individual of the training set is exposed to the predetermined light stimuli at a plurality of different occasions associated with different actual light profiles.

20. The lighting system according to claim 11, wherein to estimate the actual light profile includes to correlate the sensed body response to an unbiased ground truth comprising tagged actual light profile data.

* * * * *